(12) United States Patent
Goswami et al.

(10) Patent No.: US 8,741,342 B2
(45) Date of Patent: Jun. 3, 2014

(54) PHARMACEUTICAL COMPOSITIONS COMPRISING ENTACAPONE, LEVODOPA, AND CARBIDOPA

(75) Inventors: Sudhir Goswami, Aurangabad (IN); Mahesh Rameshwar Kalantri, Beed (IN); Asif Mohammad, Aurangabad (IN); Narayanan Murali, Chennai (IN); Girish Kumar Jain, Delhi (IN)

(73) Assignee: Wockhardt Research Centre, Chikalthana, Aurangabad O (IN)

( * ) Notice: Subject to any disclaimer, the term of this patent is extended or adjusted under 35 U.S.C. 154(b) by 640 days.

(21) Appl. No.: 12/447,405

(22) PCT Filed: Oct. 25, 2007

(86) PCT No.: PCT/IB2007/003196
§ 371 (c)(1),
(2), (4) Date: Jul. 7, 2009

(87) PCT Pub. No.: WO2008/053297
PCT Pub. Date: May 8, 2008

(65) Prior Publication Data
US 2010/0129441 A1    May 27, 2010

(30) Foreign Application Priority Data

Oct. 30, 2006  (IN) .......................... 1783/MUM/2006
Oct. 30, 2006  (IN) .......................... 1788/MUM/2006
Oct. 30, 2006  (IN) .......................... 1791/MUM/2006
Oct. 30, 2006  (IN) .......................... 1797/MUM/2006
Feb. 26, 2007  (IN) .......................... 371/MUM/2007

(51) Int. Cl.
*A61K 9/48* (2006.01)
*A61K 9/20* (2006.01)
*A61K 9/14* (2006.01)
*A61K 31/135* (2006.01)

(52) U.S. Cl.
USPC ............ 424/452; 424/465; 424/489; 514/646

(58) Field of Classification Search
USPC .......................... 424/452, 465, 489; 514/646
See application file for complete search history.

(56) References Cited

U.S. PATENT DOCUMENTS

| | | |
|---|---|---|
| 6,500,867 B1 | 12/2002 | Virkki et al. |
| 6,797,732 B2 | 9/2004 | Virkki et al. |
| 2004/0166159 A1 | 8/2004 | Han et al. |
| 2006/0222703 A1* | 10/2006 | Politi .......................... 424/464 |
| 2007/0134321 A1 | 6/2007 | Solomon et al. |

* cited by examiner

*Primary Examiner* — Renee Claytor
(74) *Attorney, Agent, or Firm* — Bio Intellectual Property Services LLC (BIO IPS); O. (Sam) Zaghmout

(57) ABSTRACT

The present invention relates to stable pharmaceutical compositions comprising entacapone, levodopa and carbidopa, or pharmaceutically acceptable salts or hydrates thereof. The invention also relates to processes for the preparation of such compositions.

13 Claims, No Drawings

PHARMACEUTICAL COMPOSITIONS COMPRISING ENTACAPONE, LEVODOPA, AND CARBIDOPA

FIELD OF THE INVENTION

The present invention relates to stable pharmaceutical compositions comprising entacapone, levodopa and carbidopa, or pharmaceutically acceptable salts or hydrates thereof. The invention also relates to processes for the preparation of such compositions.

BACKGROUND OF THE INVENTION

Entacapone, an inhibitor of catechol-O-methyltransferase (COMT), is a nitro-catechol-structured compound with a molecular weight of 305.3. It is used in the treatment of Parkinson's disease as an adjunct to levodopa/carbidopa therapy. The chemical name of entacapone is (E)-2-cyano-3-(3,4-dihydroxy-5-nitrophenyl)-N,N-diethyl-2-propenamide. Its empirical formula is $C_{14}H_{15}N_3O_5$, and its structural formula is:

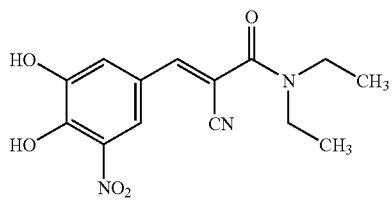 [SMILES: CCN(CC)C(=O)/C(C#N)=C/c1cc(O)c(O)c([N+](=O)[O-])c1]

Carbidopa, an inhibitor of aromatic amino acid decarboxylation, is a white, crystalline compound, slightly soluble in water, with a molecular weight of 244.3. Chemically, it is (−)-L-(α-hydrazino-(α-methyl-β-(3,4-dihydroxybenzene) propanoic acid monohydrate. Its empirical formula is $C_{10}H_{14}N_2O_4H_2O$, and its structural formula is:

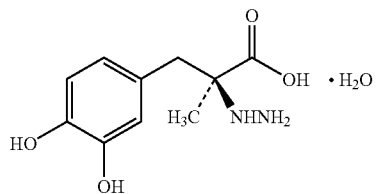 [SMILES: C[C@@](Cc1ccc(O)c(O)c1)(NN)C(=O)O ; "· H2O"]

Levodopa, an aromatic amino acid, is a white, crystalline compound, slightly soluble in water, with a molecular weight of 197.2. Chemically, it is (−)-L-α-amino-β-(3,4-dihydroxybenzene)propanoic acid. Its empirical formula is $C_9H_{11}NO_4$, and its structural formula is:

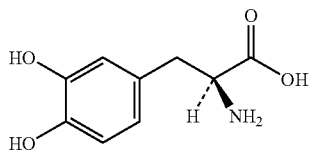 [SMILES: N[C@@H](Cc1ccc(O)c(O)c1)C(=O)O]

U.S. Pat. No. 4,963,590 discloses a pharmaceutical composition comprising entacapone and pharmaceutically acceptable carrier.

U.S. Pat. No. 6,599,530 provides an oral compacted composition in the form of a tablet, which comprises entacapone, nitecapone, or pharmaceutically acceptable salt of entacapone or nitecapone, and croscarmellose sodium in an amount of at least 6% by weight of the composition.

U.S. Pat. Nos. 6,500,867 and 6,797,732 disclose oral solid tablet compositions comprising entacapone, levodopa and carbidopa, or pharmaceutically acceptable salts or hydrates thereof, and a pharmaceutically acceptable excipient. Both these patents disclose that when carbidopa, levodopa and entacapone are mixed together, it results in stability problems and desired therapeutic effect is not achieved. On the other hand, when a substantial portion of carbidopa is separated from levodopa and entacapone, the formulation exhibits better stability and desired therapeutic effect is also achieved.

US Application No. 20060222703 describes oral pharmaceutical compositions of entacapone, carbidopa and levodopa with microcrystalline cellulose and starch by simultaneous mixing of all the three actives. The composition is prepared by compaction granulation. The application describes the disadvantages associated with wet granulation technique which includes destabilization of composition and decreased dissolution of levodopa, carbidopa and entacapone due to use of water in wet granulation method.

The present invention addresses and overcomes these commonly encountered problems.

SUMMARY OF THE INVENTION

In one general aspect there is provided a single oral dose pharmaceutical composition comprising entacapone, levodopa and carbidopa, or pharmaceutically acceptable salts or hydrates thereof, wherein a substantial portion of entacapone or a pharmaceutically acceptable salt or hydrate thereof is separated from a mixture of levodopa and carbidopa or pharmaceutically acceptable salts or hydrates thereof.

Embodiments of the pharmaceutical composition may include one or more of the following features or those described above. For example, the composition may further include one or more pharmaceutically acceptable excipients selected from fillers, lubricants, disintegrants, and glidants.

The term "substantial portion" of entacapone or pharmaceutically acceptable salts or hydrates thereof herein refers to the amount of entacapone or pharmaceutically acceptable salts or hydrates thereof that do not interfere with stability and or dissolution and therapeutic effect or bioavailability thereof in a single oral dose triple combination of entacapone, levodopa and carbidopa.

In another general aspect there is provided a single oral dose pharmaceutical composition comprising entacapone, levodopa and carbidopa, or pharmaceutically acceptable salts or hydrates thereof and microcrystalline cellulose. The pharmaceutical composition may further include one or more pharmaceutically acceptable excipients.

In another general aspect there is provided a single oral dose pharmaceutical composition comprising entacapone, levodopa and carbidopa, or pharmaceutically acceptable salts or hydrates thereof and microcrystalline cellulose, wherein the pharmaceutical composition is prepared by a wet granulation method.

Embodiments of the pharmaceutical composition may include one or more of the following features or those described above. For example, the composition may further include one or more pharmaceutically acceptable excipients selected from fillers, lubricants, disintegrants, and glidants.

In another aspect there is provided a single oral dose pharmaceutical composition comprising entacapone, levodopa and carbidopa, or pharmaceutically acceptable salts or hydrates thereof and microcrystalline cellulose, wherein a substantial portion of entacapone or a pharmaceutically acceptable salt or hydrate thereof is separated from a mixture of levodopa and carbidopa or pharmaceutically acceptable salts or hydrates thereof.

In another aspect there is provided a single oral dose pharmaceutical composition comprising entacapone, levodopa and carbidopa, or pharmaceutically acceptable salts or hydrates thereof and microcrystalline cellulose, wherein a substantial portion of carbidopa or a pharmaceutically acceptable salt or hydrate thereof is separated from a mixture of entacapone and levodopa or pharmaceutically acceptable salts or hydrates thereof.

The composition may further include one or more pharmaceutically acceptable excipients selected from fillers, lubricants, disintegrants, glidants, and the like.

The pharmaceutical compositions of the present invention can be present in the form of monolayered tablets, bilayered tablets, caplets, minitablets, capsules, tablets in a capsule, granules in a capsule, pellets, pellets in a capsule, powder, suspension or any other suitable dosage form.

In another aspect there is provided a pharmaceutical composition comprising:
a) an inner tablet comprising a mixture of levodopa and carbidopa or pharmaceutically acceptable salts or hydrates thereof optionally, with other pharmaceutically acceptable excipients; and
b) an outer tablet comprising entacapone or a pharmaceutically acceptable salt or hydrate thereof optionally, with other pharmaceutically acceptable excipients.

In another aspect there is provided a pharmaceutical composition comprising:
a) an inner tablet comprising entacapone or a pharmaceutically acceptable salt or hydrate thereof optionally, with other pharmaceutically acceptable excipients; and
b) an outer tablet comprising a mixture of levodopa and carbidopa or pharmaceutically acceptable salts or hydrates thereof optionally, with other pharmaceutically acceptable excipients.

In another aspect there is provided a single oral capsule pharmaceutical composition comprising granules of entacapone or a pharmaceutically acceptable salt or hydrate thereof optionally, with other pharmaceutically acceptable excipients and a tablet of levodopa and carbidopa or pharmaceutically acceptable salts or hydrates thereof optionally, with other pharmaceutically acceptable excipients.

In another aspect there is provided a single oral dose capsule pharmaceutical composition comprising a tablet of entacapone or a pharmaceutically acceptable salt or hydrate thereof optionally, with other pharmaceutically acceptable excipients and granules of levodopa and carbidopa or pharmaceutically acceptable salts or hydrates thereof optionally, with other pharmaceutically acceptable excipients.

In another aspect there is provided a single oral dose capsule pharmaceutical composition comprising granules of entacapone or a pharmaceutically, acceptable salt or hydrate thereof optionally, with other pharmaceutically acceptable excipients and granules of levodopa and carbidopa or pharmaceutically acceptable salts or hydrates thereof optionally, with other pharmaceutically acceptable excipients.

The pharmaceutically acceptable excipients may include one or more of fillers, lubricants, glidants, disintegrants, and the like.

The details of one or more embodiments of the inventions are set forth in the description below. Other features, objects and advantages of the inventions will be apparent from the description and claims.

DETAILED DESCRIPTION OF THE INVENTION

The inventors have now discovered that when a "substantial portion" of entacapone is separated from levodopa and carbidopa mixture in a single dose formulation, the formulation poses no stability problems and the desired therapeutic effect is achieved. The inventors also have discovered that when microcrystalline cellulose is used in a triple combination comprising entacapone, carbidopa, and levodopa, the formulation poses no stability problems on long term storage. It was also discovered that the use of a wet granulation technique neither affects the stability of formulation nor does it affect the dissolution of the formulation comprising entacapone, levodopa and carbidopa.

The pharmaceutical composition may be prepared in two parts. The first part comprises mixing entacapone with suitable fillers, granulating with a binder solution and drying the granules. The dried granules may be milled and mixed with suitable disintegrants and glidants. The granules may further be lubricated with a suitable lubricant.

The second part comprises mixing levodopa and carbidopa with suitable fillers and granulating with a binder solution. The granules may be dried. The dried granules may be milled and mixed with suitable disintegrants and glidants. The granules containing levodopa and carbidopa may further be lubricated with a suitable lubricant.

The above said granules of entacapone and the granules of levodopa and carbidopa may be formulated into a suitable dosage form. For example, they may be formulated into monolayered tablets, bilayered tablets, tablet in a tablet, a caplet, minitablets, capsules, tablet in a capsule, granules in capsules, pellets, pellets in capsules, or powder. Further, the powder or granules may be suspended to give a pharmaceutically acceptable oral suspension.

Microcrystalline cellulose is purified, partially depolymerized cellulose that occurs as white, odorless, tasteless powder composed of porous particles. It is commercially available in different particle sizes and grades, which have different properties and applications. It is widely used in pharmaceuticals primarily as a binder/diluent in oral tablet and capsule formulations. In addition to its use as a binder/diluent, it also has some lubricating and disintegrating properties. It is used as an adsorbent in a concentration range of 20-90% w/w, as an anti-adherent in a concentration range 5-20% w/w, as a capsule binder/diluent in a concentration range 20-90% w/w, as a tablet disintegrant in a concentration range 5-15% w/w and as a tablet binder/diluent in a concentration range 20-90% w/w.

The microcrystalline cellulose may be present in a concentration range from about 5% to about 90% w/w. In particular, it may be present in a concentration range from about 5% to about 50% w/w, for example from about 5% to about 20% w/w.

The pharmaceutical composition as described herein may include other pharmaceutically acceptable excipients. Examples of other pharmaceutically acceptable as used herein include binders, fillers, lubricants, disintegrants, glidants and the like.

Suitable binders may include one or more of povidone, starch, stearic acid, gums, hydroxypropylmethylcellulose, and the like.

Suitable fillers may include one or more of microcrystalline cellulose, lactose, mannitol, calcium phosphate, calcium sulfate, kaolin, dry starch, powdered sugar, and the like.

Suitable lubricants may include one or more of magnesium stearate, zinc stearate, calcium stearate, stearic acid, sodium stearyl fumarate, hydrogenated vegetable oil, and the like.

Suitable glidants may include one or more of colloidal silicon dioxide, talc or corn starch, and the like.

Suitable disintegrants may include one or more of starch, croscannellose sodium, crosspovidone, sodium starch glycolate, and the like.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

Table 1 provides the composition of batches of the present invention.

TABLE 1

| No | Ingredients | % Composition |
|---|---|---|
| | Entacapone Granules | |
| 1 | Entacapone | 28.78 |
| 2 | Microcrystalline cellulose | 5-20 |
| 3 | Mannitol | 5-25 |
| 4 | Hydroxypropyl methyl cellulose | 1-15 |
| 5 | Purified Water | q.s. |
| 6 | Croscarmellose sodium | 2-5 |
| 7 | Colloidal silicon dioxide | 0.5-2 |
| 8 | Magnesium stearate | 0.5-1.5 |
| | Levodopa, carbidopa Granules | |
| 9 | Levodopa | 21.58 |
| 10 | Carbidopa | 5.40 |
| 11 | Starch | 7-30 |
| 12 | Croscarmellose sodium | 2-5 |
| 13 | Povidone | 0.5-5 |
| 14 | Purified Water | q.s. |
| 15 | Croscarmellose sodium | 2-5 |
| 16 | Colloidal silicon dioxide | 0.5-2 |
| 17 | Magnesium stearate | 0.5-1.5 |

Procedure: The pharmaceutical composition was prepared in two parts. The first part consisted of mixing entacapone, microcrystalline cellulose and mannitol in a double cone blender, granulating with aqueous hydroxypropylmethylcellulose solution and drying the granules in a fluidized bed dryer. The dried granules were milled in a multi-mill and mixed with croscannellose sodium and colloidal silicon dioxide in a double cone blender. The granules were further lubricated with magnesium stearate in a double cone blender.

The second part, consisted of mixing levodopa, carbidopa with starch, croscarmellose sodium and granulating with an aqueous povidone solution. The granules were dried in a fluidized bed dryer. The dried granules were milled in a multi-mill and mixed with croscarmellose sodium and colloidal silicon dioxide in a double cone blender. The levodopa and carbidopa granules were further lubricated with magnesium stearate in a double cone blender.

Example 2

Table 2 provides the composition of batches of the present invention.

| No | Ingredients | % Composition |
|---|---|---|
| | Entacapone granules | |
| 1 | Entacapone | 28.78 |
| 2 | Microcrystalline cellulose | 5-20 |
| 3 | Mannitol | 5-25 |
| 4 | Hydroxypropyl methyl cellulose | 1-15 |
| 5 | Purified Water | q.s. |
| 6 | Croscarmellose sodium | 2-5 |
| 7 | Colloidal silicon dioxide | 0.5-2 |
| 8 | Magnesium stearate | 0.5-1.5 |
| | Levodopa, carbidopa granules | |
| 9 | Levodopa | 21.58 |
| 10 | Carbidopa | 5.40 |
| 11 | Starch | 7-30 |
| 12 | Croscarmellose sodium | 2-5 |
| 13 | Povidone | 0.5-5 |
| 14 | Purified Water | q.s. |
| 15 | Croscarmellose sodium | 2-5 |
| 16 | Colloidal silicon dioxide | 0.5-2 |
| 17 | Magnesium stearate | 0.5-1.5 |
| | Coating | |
| 18 | Opadry Red | 2-3 |

Procedure: The pharmaceutical composition was prepared in two parts. The first part consisted of mixing entacapone, microcrystalline cellulose and mannitol in a double cone blender, granulating with aqueous hydroxypropylmethylcellulose solution and drying the granules in a fluidized bed dryer. The dried granules were milled in a multi-mill and mixed with croscannellose sodium and colloidal silicon dioxide in a double cone blender. The entacapone granules were further lubricated with magnesium stearate in a double cone blender and either filled in hard gelatin capsules or compressed into tablets and coated with dispersion of Opadry.

The second part consisted of mixing levodopa, carbiodopa with starch, croscannellose sodium and granulating with aqueous povidone solution. The granules were dried in a fluidized bed dryer. The dried granules were milled in a multi-mill and, mixed with croscarmellose sodium and colloidal silicon dioxide in a double cone blender. The levodopa and carbidopa granules were further lubricated with magnesium stearate in a double cone blender and either filled in hard gelatin capsules or compressed into tablets and coated with dispersion of Opadry.

Finally, the entacapone tablets and levodopa and carbidopa granules were filled into hard gelatin capsules or entacapone granules and levodopa and carbidopa tablets were filled into hard gelatin capsules.

Example 3

Table 3 provides composition of batches of the present invention.

| No | Ingredients | % w/w |
|---|---|---|
| | Entacapone Granules | |
| 1 | Entacapone | 28.57 |
| 2 | Microcrystalline cellulose | 5-15 |
| 3 | Mannitol | 5-25 |
| 4 | Corn starch | 7-30 |
| 5 | Croscarmellose sodium | 2-5 |
| 6 | Polyvinylpyrrolidone | 1-5 |
| 7 | Purified Water | q.s. |

-continued

| No | Ingredients | % w/w |
|---|---|---|
| Levodopa, Carbidopa Granules | | |
| 8 | Levodopa | 21.43 |
| 9 | Carbidopa | 5.34 |
| 10 | Corn Starch | 5-40 |
| 11 | Polyvinylpyrrolidone | 1-7 |
| 12 | Purified Water | q.s. |
| 13 | Talc | 0.5-3 |
| 14 | Magnesium stearate | 0.5-1.5 |
| 15 | Opadry | 2-3 |

Procedure: The pharmaceutical composition was prepared in two parts. The first part consisted of mixing entacapone, microcrystalline cellulose, mannitol, corn starch, croscannellose sodium in a double cone blender, granulating with aqueous polyvinyl pyrrolidone (PVP) solution and drying the granules.

The second part consisted of mixing levodopa, carbidopa with corn starch, and granulating with aqueous polyvinylpyrrolidone solution. The granules were dried. The dried granules of entacapone and carbidopa and levodopa granules were mixed together in a double cone blender and further lubricated with talc and magnesium stearate in a double cone blender. The granules thus obtained were compressed into tablets and coated with aqueous dispersion of Opadry.

Example 4

Table 4 provides composition of batches of the present invention.

| No | Ingredients | % Composition |
|---|---|---|
| Entacapone granules | | |
| 1 | Entacapone | 28.57 |
| 2 | Microcrystalline cellulose | 5-20 |
| 3 | Mannitol | 5-25 |
| 4 | Povidone | 1-5 |
| 5 | Purified Water | q.s. |
| Levodopa, carbidopa granules | | |
| 6 | Levodopa | 21.43 |
| 7 | Carbidopa | 5.36 |
| 8 | Starch | 5-30 |
| 9 | Croscarmellose sodium | 1.5-5 |
| 10 | Povidone | 0.5-5 |
| 11 | Purified Water | q.s. |
| 12 | Croscarmellose sodium | 2-5 |
| 13 | Colloidal silicon dioxide | 0.5-2 |
| 14 | Hydrogenated Vegetable oil | 0.5-2 |
| 15 | Magnesium stearate | 0.5-1.5 |
| 16 | Opadry Red | 2-4 |

Procedure: The pharmaceutical composition was prepared in three parts. The first part consisted of mixing entacapone, microcrystalline cellulose and mannitol in a double cone blender, granulating with aqueous povidone solution and drying the granules in a fluidized bed dryer. The dried granules were milled using a multi-mill.

The second part was prepared by mixing levodopa and carbiodopa with starch, croscarmellose sodium and granulating with aqueous povidone solution. The granules were dried in a fluidized bed dryer and milled using a multi-mill.

The third part consisted of mixing croscarmellose sodium, colloidal silicon dioxide and hydrogenated vegetable oil with dried granules of first and second part. The final granules were lubricated with magnesium stearate and lubricated blend was compressed into tablets using suitable tooling and coated with dispersion of Opadry Red.

While the present invention has been described in terms of its specific embodiments, certain modifications and equivalents will be apparent to those skilled in the art and are intended to be included within the scope of the present invention.

We claim:

1. A wet granulated single oral dose pharmaceutical composition consisting of entacapone, levodopa and carbidopa, or pharmaceutically acceptable salts or hydrates thereof, microcrystalline cellulose and pharmaceutically acceptable excipients, wherein a substantial portion of entacapone or a pharmaceutically acceptable salt or hydrate thereof along with microcrystalline cellulose and one or more pharmaceutically acceptable excipients are separated from a mixture of levodopa and carbidopa or pharmaceutically acceptable salts or hydrates thereof along with one or more pharmaceutically acceptable excipients.

2. The pharmaceutical composition of claim 1, wherein one or more pharmaceutically acceptable excipients are selected from the group consisting of binders, fillers, lubricants, disintegrants, and glidants.

3. The pharmaceutical composition of claim 1, wherein the composition is in the form of a monolayered tablet, a bilayered tablet, a caplet, a minitablet, a capsule, a tablet in a capsule, granules in a capsule, pellets, pellets in a capsule, powder or suspension.

4. A wet granulated single oral dose capsule, pharmaceutical composition consisting of granules of entacapone or a pharmaceutically acceptable salt or hydrate thereof, microcrystalline cellulose and pharmaceutically acceptable excipients and a tablet consisting of a mixture of levodopa and carbidopa or pharmaceutically acceptable salts or hydrates thereof with other pharmaceutically acceptable excipients, wherein a substantial portion of entacapone or a pharmaceutically acceptable salt or hydrate thereof along with microcrystalline cellulose and pharmaceutically acceptable excipients are separated from the tablet consisting of a mixture of levodopa and carbidopa or pharmaceutically acceptable salts or hydrates thereof, with pharmaceutically acceptable excipients.

5. The pharmaceutical composition of claim 4, wherein the pharmaceutically acceptable excipients are selected from the group consisting of: binders, fillers, lubricants, disintegrants, and glidants.

6. A wet granulated single oral dose capsule pharmaceutical composition consisting of granules of entacapone or a pharmaceutically acceptable salt or hydrate thereof, microcrystalline cellulose and pharmaceutically acceptable excipients and granules consisting of a mixture of levodopa and carbidopa or pharmaceutically acceptable salts or hydrates thereof in combination with pharmaceutically acceptable excipients, wherein a substantial portion of the granules of entacapone or a pharmaceutically acceptable salt or hydrate thereof, microcrystalline cellulose and pharmaceutically acceptable excipients are separated from the granules comprising a mixture of levodopa and carbidopa or pharmaceutically acceptable salts or hydrates and pharmaceutically acceptable excipients.

7. The pharmaceutical composition of claim 6, wherein the pharmaceutically acceptable excipients are selected from the group consisting of: binders, fillers, lubricants, disintegrants, and glidants.

8. The single oral dose pharmaceutical composition of claim 1, obtained by separate wet granulation of entacapone and wet granulation of a mixture of levodopa and carbidopa.

9. A wet granulated monolayer single oral dose pharmaceutical composition comprising entacapone, levodopa and carbidopa, or pharmaceutically acceptable salts or hydrates thereof, and microcrystalline cellulose wherein a substantial portion of entacapone or a pharmaceutically acceptable salt or hydrate thereof and microcrystalline cellulose are separated from a mixture of levodopa and carbidopa or pharmaceutically acceptable salts or hydrates thereof, wherein pharmaceutical composition is prepared by wet granulation.

10. A wet granulated pharmaceutical composition comprising:

| No. | Ingredients | % Composition |
| --- | --- | --- |
| Entacapone Granules | | |
| 1. | Entacapone | 28.78 |
| 2. | Microcrystalline cellulose | 5-20 |
| 3. | Mannitol | 5-25 |
| 4. | Hydroxypropyl methyl cellulose | 1-15 |
| 5. | Purified water | q.s. |
| 6. | Croscarmellose sodium | 2-5 |
| 7. | Colloidal silicon dioxide | 0.5-2 |
| 8. | Magnesium stearate | 0.5-1.5 |
| Levodopa, carbidopa Granules | | |
| 9. | Levodopa | 21.58 |
| 10. | Carbidopa | 5.40 |
| 11. | Starch | 7-30 |
| 12. | Croscarmellose sodium | 2-5 |
| 13. | Povidone | 0.5-5 |
| 14. | Purified water | q.s. |
| 15. | Corcarmellose sodium | 2-5 |
| 16. | Colloidal silicon dioxide | 0.5-2 |
| 17. | Magnesium stearate | 0.5-1.5. |

11. A wet granulated pharmaceutical composition comprising:

| No. | Ingredients | % Composition |
| --- | --- | --- |
| Entacapone granules | | |
| 1. | Entacapone | 28.78 |
| 2. | Microcrystalline cellulose | 5-20 |
| 3. | Mannitol | 5-25 |
| 4. | Hydroxypropyl methyl cellulose | 1-15 |
| 5. | Purified water | q.s |
| 6. | Croscarmellose sodium | 2-5 |
| 7. | Colloidal silicon dioxide | 0.5-2 |
| 8. | Magnesium stearate | 0.5-1.5 |
| Levodopa, carbidopa granules | | |
| 9. | Levodopa | 21.58 |
| 10. | Carbidopa | 5.40 |
| 11. | Starch | 7-30 |
| 12. | Croscarmellose sodium | 2-5 |
| 13. | Povidone | 0.5-5 |
| 14. | Purified water | q.s. |
| 15. | Croscarmellose sodium | 2-5 |
| 16. | Colloidal silicon dioxide | 0.5-2 |
| 17. | Magnesium stearate | 0.5-1.5 |
| Coating | | |
| 18. | Opadry red | 2-3. |

12. A wet granulated pharmaceutical composition comprising:

| No | Ingredients | % w/w |
| --- | --- | --- |
| Entacapone granules | | |
| 1. | Entacapone | 28.57 |
| 2. | Microcrystalline cellulose | 5-15 |
| 3. | Mannitol | 5-25 |
| 4. | Corn starch | 7-30 |
| 5. | Croscarmellose sodium | 2-5 |
| 6. | Polyvinylpyrrolidone | 1-5 |
| 7. | Purified water | q.s. |
| Levodopa, carbidopa granules | | |
| 8. | Levodopa | 21.43 |
| 9. | Carbidopa | 5.34 |
| 10. | Corn starch | 5-40 |
| 11. | Polyvinylpyrrolidone | 1-7 |
| 12. | Purified water | q.s. |
| 13. | Talc | 0.5-3 |
| 14. | Magnesium stearate | 0.5-1.5 |
| 15. | Opadry | 2-3. |

13. A wet granulated pharmaceutical composition comprising:

| No. | Ingredients | % Composition |
| --- | --- | --- |
| Entacapone granules | | |
| 1. | Entacapone | 28.57 |
| 2. | Microcrystalline cellulose | 5-20 |
| 3. | Mannitol | 5-25 |
| 4. | Povidone | 1-5 |
| 5 | Purified water | q.s. |
| Levodopa, carbidopa granules | | |
| 6. | Levodopa | 21.43 |
| 7. | Carbidopa | 5.36 |
| 8. | Starch | 5-30 |
| 9. | Croscarmellose sodium | 1.5-5 |
| 10. | Povidone | 0.5-5 |
| 11. | Purified water | q.s. |
| 12. | Croscarmellose sodium | 2-5 |
| 13. | Colloidal silicon dioxide | 0.5-2 |
| 14. | Hydrogenated vegetable oil | 0.5-2 |
| 15. | Magnesium stearate | 0.5-1.5 |
| 16. | Opadry red | 2-4. |

\* \* \* \* \*